United States Patent [19]
Valerino, Sr.

[11] Patent Number: 6,048,086
[45] Date of Patent: Apr. 11, 2000

[54] PARENTERAL PRODUCTS AUTOMATIC SYSTEM (PPAS) WITH AN ORAL/SOLID INTERFACE

[76] Inventor: Fred M. Valerino, Sr., 327 Gailridge Rd., Timonium, Md. 21093

[21] Appl. No.: 08/935,090

[22] Filed: Sep. 25, 1997

Related U.S. Application Data

[63] Continuation-in-part of application No. 08/513,569, Aug. 10, 1995, Pat. No. 5,805,454.

[51] Int. Cl.$^7$ .............................. G06F 17/00; G06G 7/48
[52] U.S. Cl. .............. 364/478.03; 364/131; 364/474.15; 395/82; 395/84; 514/60; 514/474
[58] Field of Search .............................. 364/478.03, 131, 364/474.15; 395/82, 84, 92; 514/474, 60; 221/211; 406/1, 186; 901/31, 32, 33, 34, 35

[56] References Cited

U.S. PATENT DOCUMENTS

| | | | |
|---|---|---|---|
| 3,822,025 | 7/1974 | Loos | 214/16.4 |
| 5,217,328 | 6/1993 | Lang | 406/1 |
| 5,725,124 | 3/1998 | Bustos et al. | 221/211 |

*Primary Examiner*—William Grant
*Assistant Examiner*—McDieunel Marc
*Attorney, Agent, or Firm*—Ward & Olivo

[57] ABSTRACT

The present invention relates to an automated system for the retrieval and delivery of oral/solid and parenteral products from a central pharmacy supply or other location to predetermined destinations within a hospital comprising robot devices and a pneumatic tube carrier system. The system comprises an input queue, a dispensing apparatus comprising a robot device and a number of stations from which the robot device works, an inspection station, and a transportation system. A computer interface provides bi-directional communication between analytical instruments, robots and peripheral devices and a computer. The robot employed by the system is responsive to computer commands and capable of performing mechanical functions including selection and retrieval of necessary items, and manipulation of retrieved items such that desired product is delivered. For oral/solid products, the item(s) is(are) automatically retrieved by a robotic device, moved to a transportation device, such as a pneumatic tube carrier, which is automatically opened and positioned to receive the product, automatically inserted into (or onto) the transportation device, and automatically delivered to its predetermined destination.

10 Claims, 12 Drawing Sheets

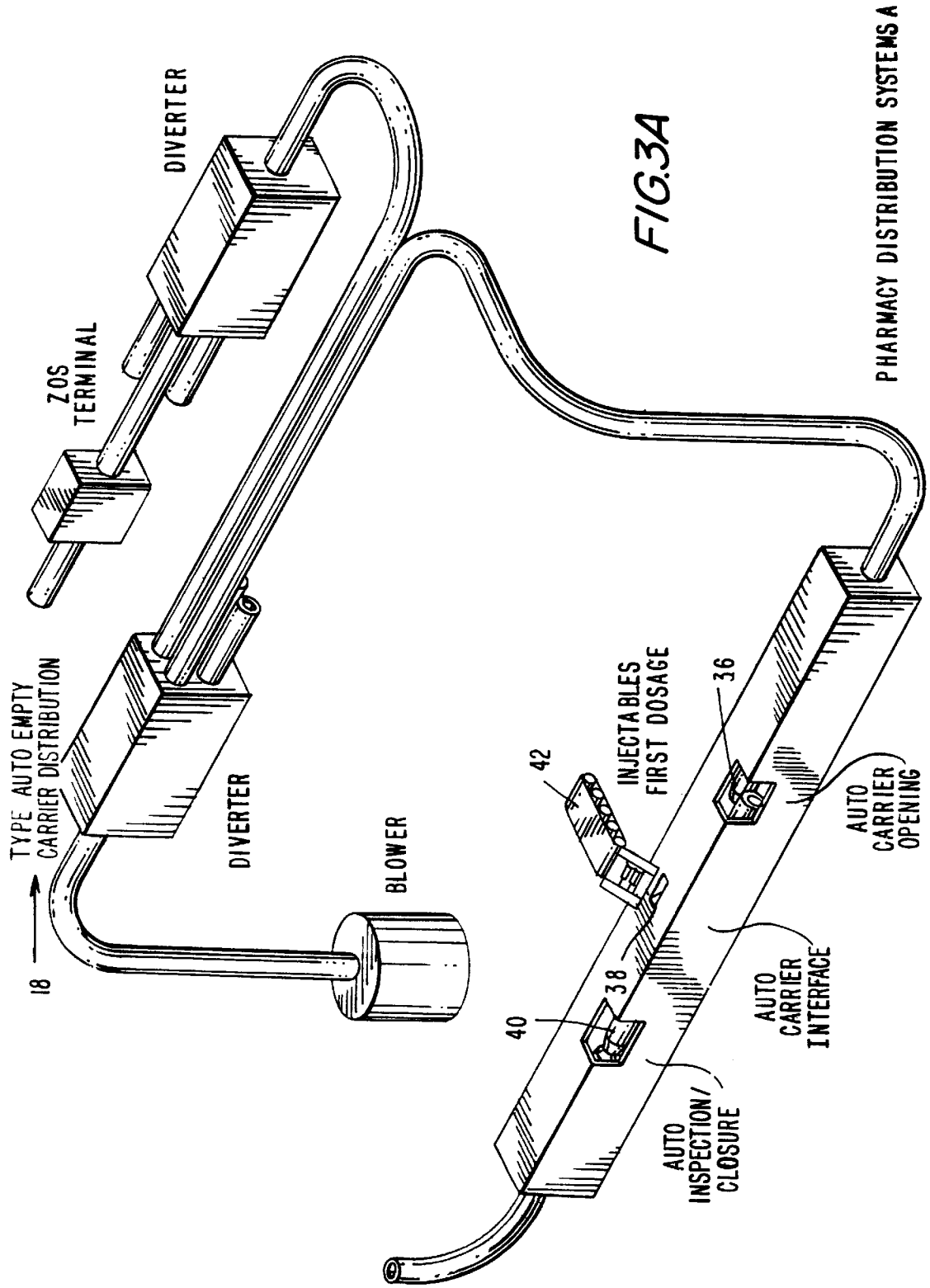

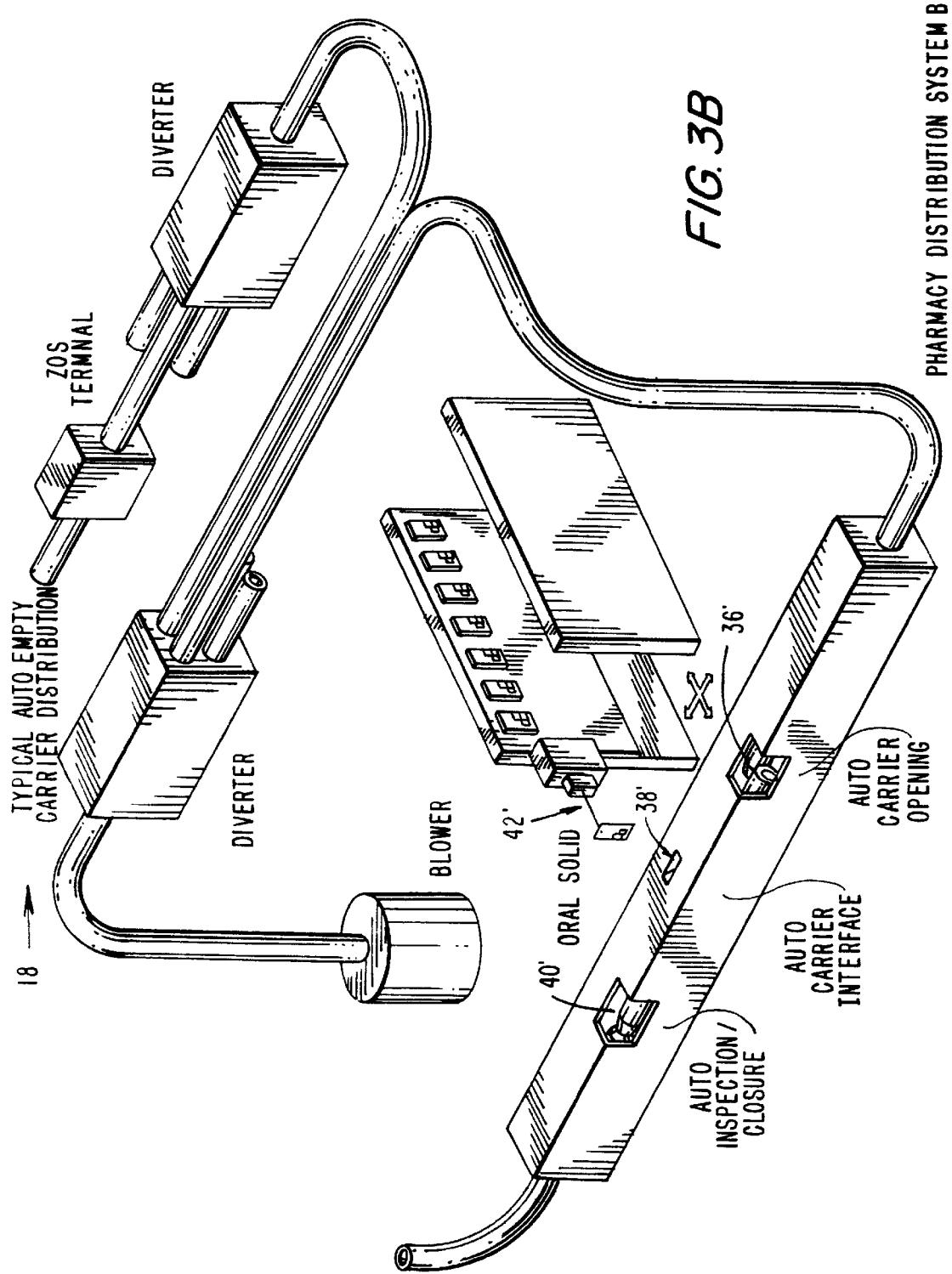

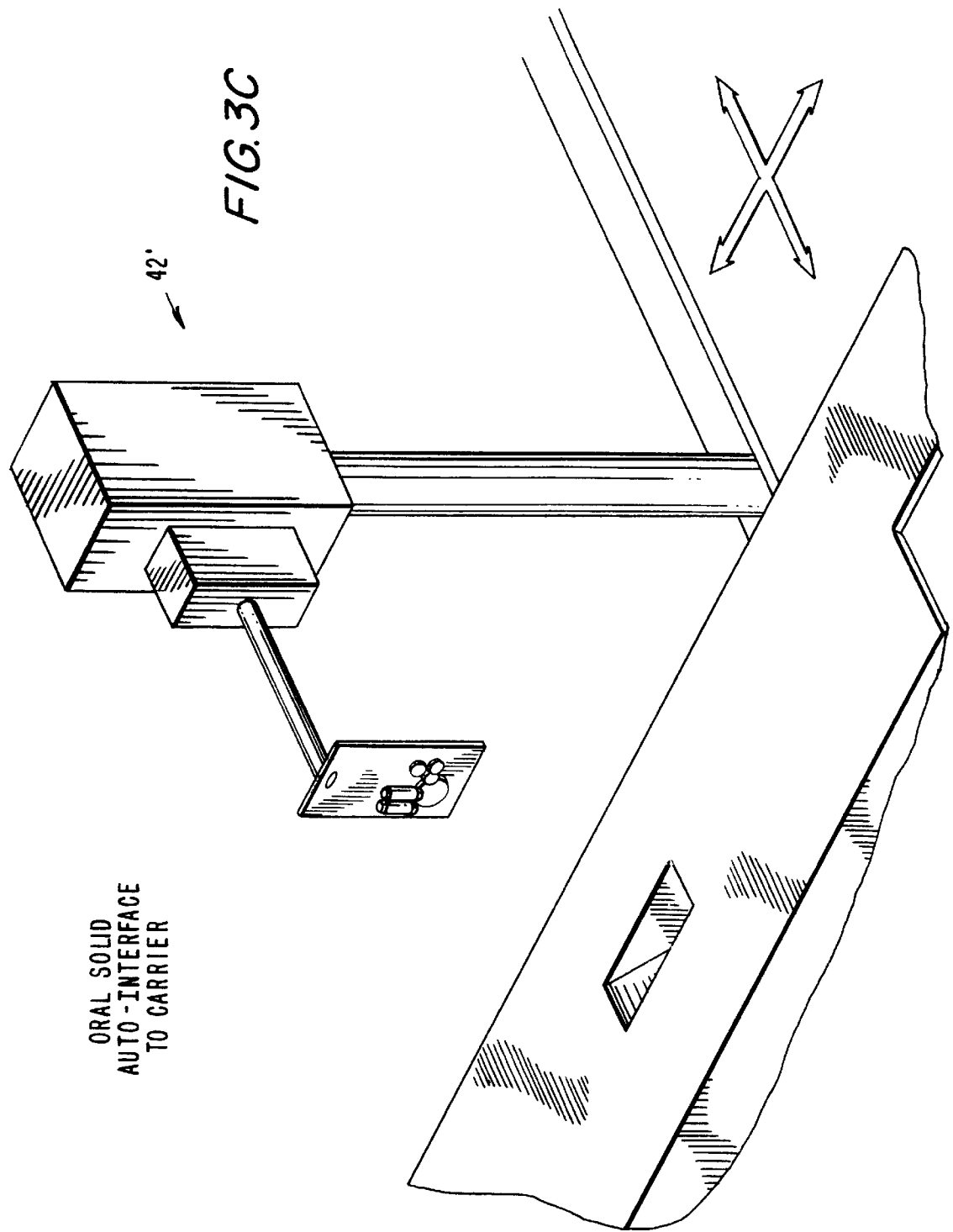

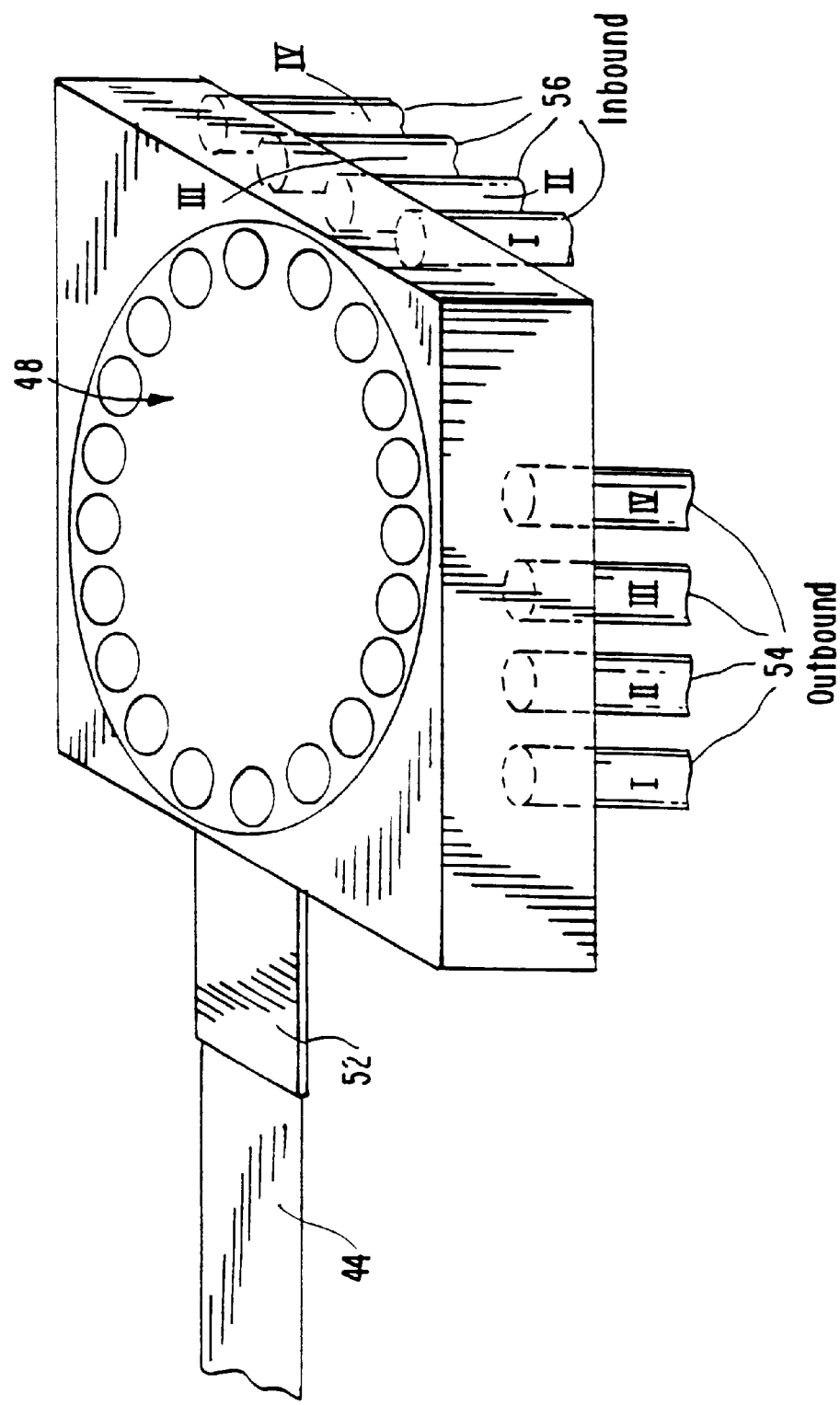

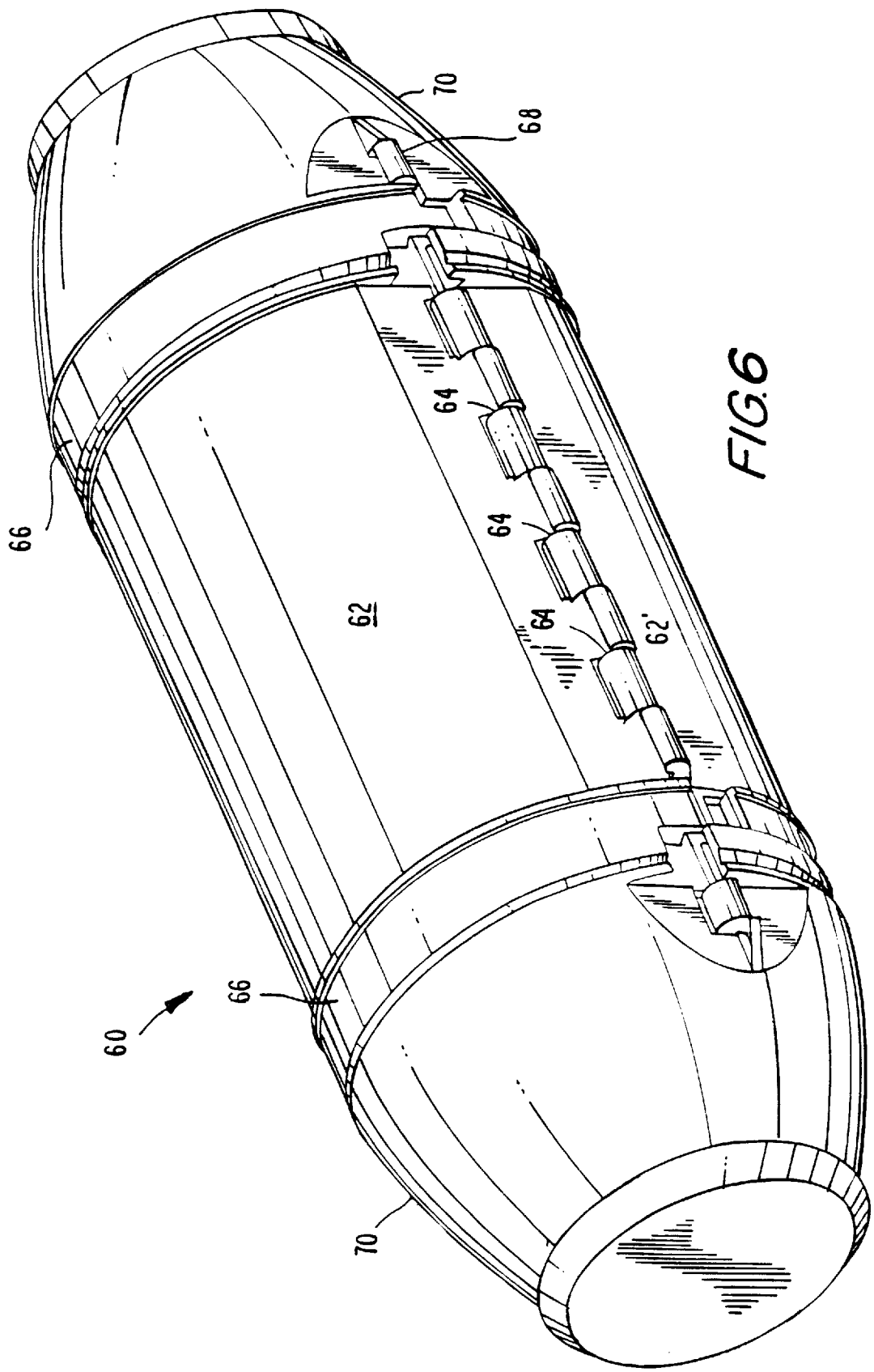

PARENTERAL PRODUCTS AUTOMATIC SYSTEM (PPAS) WITH AN ORAL/SOLID INTERFACE

CROSS-REFERENCE TO RELATED APPLICATIONS

This application is a continuation-in-part of application Ser. No. 08/513,569, filed Aug. 10, 1995. Now U.S. Pat. No. 5,805,454.

TECHNICAL FIELD

The present invention relates to an automated system for the preparation and delivery of oral/solid and parenteral products from a hospital pharmacy, dietary, laboratory, or central supply to a variety of predetermined stations within a hospital, utilizing robot devices and pneumatic tube carriers. The system comprises a four-step process including the following: a queue input step; a product preparation step; a product inspection step; and a transport step. This invention utilizes a robotics selection, reconstitution, and dispensing apparatus in conjunction with a pneumatic tube system for preparing and transporting oral/solid and parenteral products accurately and efficiently.

In many hospitals large numbers of doses of oral/solid products and parenteral products have to be prepared daily, such as pills, intravenous bags and other medications administered either orally or intravenously. These doses are usually prepared manually in what is an exacting but tedious responsibility for a highly skilled staff. It is, therefore, an object of this invention to provide an automated dispenser to simplify the manual operations necessary for preparing doses of oral/solid and parenteral products while maintaining the exacting standards set by medical regulatory bodies.

Further, prompt and reliable delivery of these oral/solid and parenteral products to the patient is essential to the daily operations of a hospital. Manual delivery can be slow and unreliable, possibly resulting in harm to patients. Pneumatic tube transportation systems are currently used to transfer blood samples, medicines, intravenous bags, viral samples or other biological or chemical matter between locations within a hospital or laboratory quickly and reliably. Thus, it is an object of this invention to combine the pneumatic tube system with a robot device apparatus to provide a complete automated system for the efficient processing and delivery of oral/solid and parenteral products within a hospital. Other uses of the present invention include dietary, laboratory, and central supply systems, as well as to prepare and deliver intravenous bags.

BACKGROUND OF THE INVENTION

According to the invention there is provided an automated system comprising processing, inspection, and transportation stations for the preparation and delivery of oral/solid and parenteral products to a plurality of stations within a hospital. The system comprises several methods which are currently in the market place. The automated processing of pharmaceutical products via robot devices is not new. Presently employed are robot devices having gripping means presentable to a plurality of stations, each station being adapted to cooperate with the robot device in a sequence of operations such as to produce a measured pharmaceutical dose from a supply of a pharmaceutically acceptable substances, and one of the stations comprising means for locating in parallel a plurality of medical hypodermic syringes for containing a said substance and for operating said syringe. The substance might comprise a medication to be administered to a patient (either orally or intravenously), or a potentially biologically damaging substance, such as a radionuclide or a cytotoxin. The measured dose might be retained in a said syringe, or in a medical vial. Preferably, means are provided for controlling the apparatus in a predetermined sequence of operations.

Sterility is an essential characteristic of injectable and ophthalmic pharmaceutical products. This characteristic is imparted to the product by virtue of the type of manufacturing process. If during the process, all components, solutions and equipment are pre-sterilized and assembled aseptically, that is, using techniques which exclude microorganisms, the product is deemed an "aseptic fill". Other injectable products, in addition to the aseptic processing, undergo sterilization when in the final container, typically using steam under pressure. This procedure, if properly designed and executed, results in a terminally sterilized product.

One solution to the problems incurred through human contamination is through automation of the processing procedure. A paper entitled, "A Robotics System for the Sterility Testing of Injectables," Barbara J. Zlotnick and Michael L. Franklin, Pharmaceutical Technology, May 1987, describes a robotics system for sterility testing of vials. According to this paper a robot is used to perform sterility testing and minimize the manipulations performed by the analyst, thereby reducing the potential for technical contamination attributable to personnel. Since human intervention is minimized during testing, the environment of the test remains cleaner with respect to viable particulate matter. There is a lower level of human activity and less potential for contamination from shedding or from disruption of the laminarity of the air flow under the hood. A cleaner environment can then be used for a greater proportion of the work day.

In general, robotics dispensing devices known in the art include a dispensing apparatus comprising a base, and a robot device on the base. A number of stations are located on the base which cooperate with the robot device in a sequence of operations such as to produce a measured pharmaceutical dose from a supply of pharmaceutically acceptable substances. Robotics dispensing apparatus systems are used for the rapid and efficient processing of a wide variety of pharmaceutical products, as well as perform various mechanical functions. Further, use of the robot device provides an efficient manner in which to maintain a sterile environment to produce the pharmaceutical products.

The transporting of articles via pneumatic tubes is old and well known. Basically, an object is placed within a container which is then transported by air under either positive or negative pressure from one destination to another. The transport is moved within a closed tube. The interior of the closed tube and the outer dimension of the carrier form a seal, so that the carrier can be propelled between the destinations by a vacuum.

In general, pneumatic tube systems known in the art include a closed continuous passageway having a predetermined inner cross-sectional dimension where the passageway includes a plurality of curves or bends having a predetermined radius. A fluid, such as air, is controllably forced through the passageway in a loop to move a carrier through the passageway. In order for the carrier to move freely through the passageway, the dimensions, and in particular the length, of the carriers being used have been limited by the inner cross-sectional dimension and curvature radius of the passageway. Pneumatic delivery systems are used extensively for the rapid and efficient transportation of a wide variety of articles. These delivery systems are used in a number of business operations, including banks, hospitals, office buildings, industrial plants, and truck terminals as a few examples.

One area of commerce which currently uses the pneumatic tube and the transporting of material via the pneumatic tube on a fairly regular basis is the hospital or biomedical research/manufacturing industry. One particular application of this technology is in the area of transporting oral pharmaceuticals, blood samples, medicines, intravenous bags, viral samples or other biological or chemical matter between locations within a hospital or laboratory.

In that environment, for example, test tubes or vials of liquids are placed within a tube carrier, and are typically secured by foam or clamps within the carrier. The purpose of securing the samples (which are often contained within glass test tubes with rubber stoppers) is to help prevent breakage. When glass breaks or stoppers become dislodged (as can happen when hospital workers fail to properly secure the stoppers in the first place), chemical or biological substances can leak into the interior of the carrier. In turn, said substances can leak out of the interior of the carrier, thereby contaminating the interior walls of the tube system.

The vials or vessels of liquids, solids or gasses within the carrier can move or shift during transport, which can also lead to breakage. This problem is especially acute, as the carriers are often travelling at speeds in excess of 25 feet per second. Because of the rapid acceleration and deceleration of pneumatic tube carriers, the carrier contents can easily become dislodged, and can break within the carrier, if not for clamps, foam securing means, and other similar securing mechanisms. Nonetheless, accidents can happen, whereby despite the best efforts toward securing or protecting the interior vessels, they can break, or their stoppers can become dislodged. In fact, dislodged stoppers are a primary problem, due mainly to workers who may inadvertently fail to secure them properly in the first place.

If the leaking substance is of a sufficient quantity, the substance (often a fluid) can leak out of the carrier. In that case, the entire tube transport system could become contaminated with the substance. For example, if fluids containing a virus or bacteria sample (for example, the HIV virus or the Ebola bacteria) were to leak out of a carrier, the interior of the vacuum transport tubes could become breeding grounds for the biological specimens—thus contaminating the exteriors of all carriers that pass through the system. Also equally important is that fluids escaping from the carrier can "gum up" the interior of the vacuum tubes, making the smooth passage of the carrier difficult, resulting in enhanced downtime, increased maintenance expense, and increased power consumption (that is, friction would increase within the tube system).

Of course, other problems can result. For example, a hospital worker may cut his or her hands on a broken vial or syringe when they proceed to open the carrier, and dangerous substances contained within the carrier may come in contact with the hospital worker. Also, in the case where toxic, aromatic substances such as toluene or benzene are being transported within vessels contained within the carriers, obviously, the worker would be placed in great danger if he or she opened the carrier under those circumstances. Basically, if a hospital worker opens a carrier expecting to remove sealed vessels and/or containers, and conversely, is presented with spilled contents (which may often be accompanied by broken glass, for example), then, the possibility of infecting the hospital worker or the overall tube system is great. For that reason, a watertight or airtight carrier could facilitate containing the hazardous substances within the carrier, so that vessels that may break or become unsealed in the transport process are contained within the carrier. Of course, problems can still result if workers open a carrier without knowledge of the hazardous circumstances within. To safeguard against that event, the carrier could contain an indicator on its exterior that notifies the carrier handler of the interior circumstances—before the carrier is opened. In that case, if the interior contents are, for example, toxic gasses, the carrier may be opened in a controlled, safe environment.

It is preferable in the present invention to use in the pneumatic tube system a carrier with suitable watertight and airtight properties, such that matter from within the carrier cannot escape to the outside, and matter that has become uncontrollable within the carrier can activate a warning indicator on the exterior of the carrier, so that hospital or other workers who use the carriers will not open carriers with uncontrolled contents (without ample warning that proper measures should be taken). That could be facilitated by a warning signal indicative of a spill or other abnormal condition within the carrier. Such a warning signal may even be a digital output, which can be decoded, to indicate what type of hazard lies within the carrier. Such a warning signal could also trigger a locking mechanism, making the opening of a carrier with spilled interior substances impossible, without authorization and a form of key, electronic or otherwise. Also, based on the contents of the carrier, the locking mechanism may be activated so that only certain parties may be able to open the carrier, regardless of whether an uncontrolled substance is contained within. For example, if a dangerous controlled substance such as morphine is being transported, the carrier may be locked, and only certain authorized persons would be able to open the carrier.

Pneumatic carriers for use in such pneumatic tube systems come in a wide range of sizes and shapes to accommodate the physical articles to be transported in the system. As an example, pneumatic carriers are provided for transporting cash, messages, stock transaction slips, letters, blueprints, electronic data processing cards, x-rays, pharmaceutical supplies, blood samples, narcotics, viral and bacteria cultures, and a variety of other small physical objects.

In the past, various mechanisms have been utilized as closure devices for pneumatic tube carriers. For example, many such carriers include an end cap that is hinged with respect to a cylindrical hull on one side of the hull and which has a latch that fastens the end cap to the opposite side of the hull in a closed position. Such carriers employ a variety of fasteners, such as snap fasteners, elastic straps with holes that fit over hooks, or straps that may be secured to bendable posts.

Other types of pneumatic tube carriers are of the side opening variety. One conventional form of such a carrier employs two generally semi-cylindrical sections that are hinged along one longitudinal edge. The hinged sections may be swung toward or away from each other to effectuate opening and closing of the carrier hull. Locking is achieved by virtue of the end caps, which may be twisted to effectuate threaded engagement of the caps onto the carrier hull ends when the hinged hull sections have been closed. That is, the end caps are rotated in such a fashion as to be drawn towards each other onto the ends of the hull, thereby immobilizing the hull sections relative to each other. Rotation of the end caps in the opposite direction releases the hull sections and allows them to be opened.

One preferable configuration is that of a side opening, wherein the two sides are hinged together, and the two sides are held together when the carrier is closed by use of a hook, or detent or indented type locking lip. Such carriers include latching mechanisms to prevent the door from coming ajar or opening during transit, which could cause the carrier to become lodged in the pneumatic tubes and would also allow the contents of the carrier to spill out into the tube system. In addition, the instructions for latching such side opening containers or carriers are simple to follow, so that the container can be easily placed within the tube system. Such hinging and locking mechanisms make waterproofing or sealing the carrier a particularly difficult task, as the hinges and locks are embedded within the mold of the carrier, which is generally formed of plastic.

In another type of side opening pneumatic carrier, the access to the carrier is gained by simultaneously pulling and twisting the ends of the carrier to allow the side opening door to be opened. The instructions for such a two-step process are often difficult for many users to follow, and the physical effort and manual dexterity needed to simultaneously pull and twist both ends of the carrier against a spring resistance is often troublesome for many hospital workers.

The present invention displays a preference for a pneumatic carrier which can be easily opened, but which also maintains a watertight and airtight seal. Also, the carrier should be able to maintain its air and water tightness, despite the fact that it is subjected to a vacuum transport system, and despite the fact that it will be subjected to extreme environmental conditions, such as repeated use, frequent drops, dust and dirt particles, high speed travel and acceleration, and other similar conditions. The carrier should also have a supplemental sensor mechanism to indicate that abnormal interior conditions have developed.

SUMMARY OF THE INVENTION

The invention relates to a four-step automated system for the preparation and transportation, through a pneumatic tube system, of pharmaceutical products (both oral/solid and parenteral) to any of a variety of predetermined locations within a hospital, such as nurses' stations. As an alternative, the invention could be made to deliver the parenteral products directly to the patient's room.

The system comprises an input queue, a dispensing apparatus comprising a robot device and a plurality of stations from which the robot device works, an inspection station, and a loading station which places the product into the pneumatic tube system. A computer interface provides bi-directional communication between analytical instruments, robots, and peripheral devices and a computer. The robot employed by the system is responsive to computer commands and capable of performing mechanical functions including selection and retrieval of the necessary item (i.e., drug vial, syringe, etc.) and manipulation of retrieved items such that the desired product is prepared.

The system described will receive its instructions from an interface established between PPAS and the Pharmacy Information System present at the facility where the invention is in place. These instructions are communicated to the processing station comprising a robotics device and a plurality of work stations. The robotics device, utilizing weigh stations for quality control, retrieves a drug dosage vial, reconstitutes the powdered drug dosage of the drug, agitates it to effect a complete dissolving of the product in the added diluent, affixes a syringe tip-cap to the diluted product, and labels the final prepared product. The product is transported via a conveyor belt to an inspection station where all of the products are inspected to assure an accurately prepared product. The inspection methods comprise either manual or automatic inspection. Possible automatic inspection include gas chromatography, specific gravity testing, barcode scanning, etc.

From the inspection station, via conveyor belt, the product enters a staging area for the pneumatic tube system, which determines the appropriate station to send the product based upon information provided on the label affixed to the syringe. There it is automatically loaded into a carrier, which is assigned a discreet identifier, inserted into the appropriate tube, and routed to the correct location. When the carrier is removed from the receiving station the production cycle is ended.

The control system database is capable of being searched to determine the status of any single parenteral product being prepared. The overall throughput of the system should be approximately 50 units per hour, with no more than 1 hour of downtime required per day for maintenance, supply replenishment, cleaning, etc.

Step one involves the input to the control system via transfer of a file which is prepared within the Pharmacy Information System used in the facility being automated. Based on the patient information in the Pharmacy Information System, a computer automatically sends requests to the control system for the preparation and delivery of the proper pharmaceutical product to the appropriate location at the time it is to be administered to the patient. These files are commonly used within the Pharmacy Information System to batch production requirements into a grouping of parenteral products required for a precise period of time. This time period can usually be defined by the facility and can be varied to meet its needs. The contents of this file might include the following database elements which may be used by control system:

1. Name, strength, and diluent of drug;
2. Name of patient for whom the product is intended;
3. Room number location of patient;
4. Label instructions and notes; and
5. Time the product is due for administration. Barcodes could be used to provide any of the above mentioned information upon scanning, thus, enabling the control system database to be searched to determine the status of any product at any time during its preparation and transportation. Further, the system could allow for manual requests, input at any of a plurality of computer terminals within the hospital.

Step two of the invention is the product preparation stage which involves a series of manipulations performed by the robotics arm or arms resulting in the preparation of a single intravenous product unit or oral/solid product unit based on the information provided to the control system in step one. The robotics arm or arms should be situated such that it can access any of the plurality of stations from which it performs the product preparation.

For oral/solid products, the series of manipulations are as follows:

The oral/solid drug specified is retrieved by a robotics arm from a gravity feed rack which was hand-fed prior to the initiation of the automated preparation. A sensor should be placed at the end of each column of drug storage to detect an empty rack and thus notify the operation system that the column needs to be replenished. As an alternative, inventory control software could manage the number of units present in the supply rack or column.

Upon retrieval of the proper drug vial by the robotics arm, the protective cap is removed by inserting the vial into a jig and snapping off the protective cap. The robotics arm then moves to another station where the appropriate dosage of oral/solid drug can be determined, for example, by weight, quantity, etc., and such dosage is removed from the vial via the robotic arm. The proper dosage is then placed into a delivery container and sent to the inspection area via a conveyor.

At this point the system should be able to start on the next drug. This is important to maintain the productivity of the unit at a high level of output.

For intravenous products, the series of manipulations are as follows:

The drug specified is retrieved by a robotics arm from a gravity feed rack which was hand-fed prior to the initiation of the automated preparation. A sensor should be placed at the end of each column of drug storage to detect an empty rack and thus notify the operation system that the column needs to be replenished. As an alternative, inventory control software could manage the number of units present in the supply rack or column.

Upon retrieval of the correct drug vial by the robotics arm, the protective cap is removed by inserting the vial into a jig and snapping off the protective cap. The exposed rubber stopper of the vial is swabbed on an alcohol impregnated cotton pledget station. The pledget remains moist with isopropyl alcohol due to a wicking action. Prior to start up of the system, the alcohol container must be filled.

After cleaning the stopper with alcohol, the robotics arm is to set the vial down and retrieve from a syringe rack a standard syringe with a needle attached. The arm then removes the protective needle cover by sticking the cap in a jig and pulling straight up. This action exposes the needle, and the protective cap is discarded.

Next the robotics arm moves to another station and inserts the needle into the injection port of a bag of Sterile Water for Injection which is held inverted, and must be changed with every 100 units prepared. The system must notify the operator to change this unit at the appropriate time. For example, inventory control software could keep track of the units prepared. After insertion of the needle, the plunger on the syringe is extracted drawing water into the syringe.

The syringe and needle containing the water is extracted from the Sterile Water for Injection bag. The regular needle is discarded in a Sharps Waste Container at another station and a vented needle is retrieved from a rack and placed on the end of the syringe. The robotics arm returns to the drug vial where it inserts the syringe into the selected vial of drug. The plunger of the syringe is depressed, expelling the Sterile Water for Injection into the drug vial. Once completely emptied, the syringe and vented needle are removed, and the vial and diluent are placed on an agitation table for 60 seconds.

At this point the system should be able to start on the next drug while waiting for the current drug to complete the agitation step. This is important to maintain the productivity of the unit at a high level of output. Also, the agitation table can be divided into four zones, with each zone being designated within the operating system.

Upon completion of agitation, the robotics arm removes the drug vial from its zone of the agitation table and places it upon a compounding counter. The arm then retrieves the appropriate syringe with vented needle, and inserts the needle into the vial of the drug in solution. The complete, attached system of drug vial, syringe and needle is inverted with the syringe pointing upward. The plunger is retracted, thereby withdrawing the entire contents of the drug vial back into the syringe. The syringe and vented needle are removed from the empty drug vial, and the empty vial is placed in a transport bin, which is gravity fed to a staging location adjacent to a conveyor belt.

The robotics arm removes the vented needle from the syringe. This needle is placed in a Sharps Waste Container. The syringe is inverted and a syringe tip cap is placed on its end. The reconstituted drug within the syringe is then labeled by rolling it over the labeling unit.

The syringe containing the reconstituted and labeled drug is then weighed to assure that the unit meets anticipated specifications for weight, assuring that all diluent was added and all of the drug extracted into the syringe. If accepted, the drug is placed in the same transport bin as the empty drug vial, and the transport bin is slid onto the conveyor belt which transporting the product to the inspection station.

In use of the dispenser, (e.g. for obtaining a dose of Technetium 99 m), syringes, needles, needle caps, vials, etc. are stored on racks with sensors to detect empty racks.

If dose dilution is required, saline solution may be withdrawn from an appropriate vial by use of the syringe, and then inserted into a required vial.

It will be understood that if desired the assembly may be modified to accept two, or more syringes, and may be operated in an alternative manner from that described above. For instance, the above described manipulations performed by the robot arm may alternatively be performed individually at each work station while a means is provided to move the product from one station to the next.

Step three represents the manual or automatic inspection procedure incorporated into this invention. It sits midway between the preparation station and the transportation station. The resultant drug product will be visually inspected for particular matter, proper labeling, and matching of the drug vial to the stated contents on the label of the syringe. If all is correct, the product will be initialed by the inspecting pharmacist, and placed back on the conveyor for transportation to the transportation system. The transport bin will be returned to the rack feeding the robotics arm, and the empty drug vial will be discarded.

For a preferable automated inspection procedure, a few alternatives are available: barcode scanning; specific gravity reading; and gas chromatography. Barcode scanning represents an automated method not unlike the manual inspection (i.e., reading and comparing the labels of the vial and product). Reading the specific gravity of the product allows the system to determine the constitution of the product, with which the system can determine whether it is correct or incorrect. Gas chromatography produces similar results as the specific gravity reading through detecting the prior contents of the empty vial and detecting the constitution of the syringe product.

Step four of the present invention relates to a computerized pneumatic tube transport system consisting of stations, diverters, a blower package and a computer, all connected via single transmission tubing. It is an object of this invention to provide a traditional pneumatic system in conjunction with the automated preparation step to provide a completely automated pharmaceutical preparation and delivery system within a hospital. The conventional pneumatic tube systems are designed to accommodate carriers of conventional design with a length limited by the predetermined curvature radius of the passageways.

The pneumatic tube system could be divided into a four zone system with each zone having its own inbound and outbound tubes. Within each zone are a plurality of receiving stations which are all connected via a series of diverters. The diverters also connect the various zones, allowing inter-zone transportation.

The product is transported from the inspection station to a loading dock via conveyor belt. This step could comprise a carousel style loading station whereby a fifty carrier carousel rotates past the loading dock. The carrier is presented to the loading station in a closed position where photo eyes verify that the carrier is the appropriate style carrier, that the carrier has an insert, and that the carrier insert is empty. If verified, the product is inserted into the empty carrier (via robotic arm) which is then inserted into an open carousel member which transports it to the proper zone's pneumatic tube. If rejected, the carousel rotates so the photo eyes can check the next carrier. This continues until a useful carrier is detected. The system could notify the control system of the reject status of the carrier. The carriers could be numbered or otherwise labeled to avoid confusion and to simplify correction of problematic carriers.

Once the product and carrier are loaded, the carousel rotates to the appropriate outbound pneumatic tube. Four of such tubes could be used in this invention, one for each zone in the system. The carrier is then inserted into the tube and then sent to its predetermined destination. A series of diverters present in the system allow inter-zone communication, thus allowing the pneumatic tube system to be used for station to station delivery.

The carrier includes two semi-cylindrical mating, elongated members. The two semi-cylindrical members include means for securing the members to each other to provide a closed elongated compartment, each of the members having an outer cross-sectional dimension which is smaller than the inner cross-sectional dimension of the passageway so that the elongated compartment can pass through the curves of the pneumatic system without engaging the inner surface of the passageway, and each of the members further including means for engaging the inner surface of the passageway to accelerate and stabilize the compartment within the passageway, the surface-engaging means having an outer cross-sectional dimension which is generally equal to the predetermined inner cross-sectional dimension of the passageway. A supplemental ring can be installed around the circumference of the carrier (that is, the two semi-cylindrical in their mated, closed position), to provide an enhanced pressure barrier, to help the carrier move throughout the tube system.

The exterior surface of the carrier may include one or more accelerator rings formed on the perimeter of both members. The accelerator rings have an outer cross-sectional dimension which allows it to engage the inner surface of the passageway to provide stability to the carrier and allow the carrier to be moved in response to the controlled air pressure within the passageway. Each of the accelerator rings has a small width in relationship to the overall length of the closed elongated compartment, and each is located in proximity to the ends of the first and second members.

Further, the carrier should be a relatively easy to open carrier which cannot be inserted into the pneumatic tube delivery system in the partially opened condition. The pneumatic carrier will typically be constructed of plastic, and will contain means to secure articles within the carrier during travel. For example, if, as in the present invention, the carrier is used to transport biomedical or chemical materials, many of which could be dangerous, the carrier will contain either, preferably, a series of clips to retain syringes, or alternatively, a formed foam rubber insert, that can be slotted, egg crate shaped, formed with slits or other cavities in any shape or size, including being formed with holes which mate with syringes, circular openings, and so on, so that the materials contained within the carrier are secured to minimize breakage. In addition, the pneumatic carrier is designed to prevent opening of the carrier once it is in transit in the pneumatic tube delivery system. A lock should be incorporated for that purpose.

Also, the carrier includes means for securing the shells in the closed position. A raised area on the external face of each of the internal closure pieces, and an indented area is formed in the internal face of the external closure pieces, such that the raised and reciprocal indented areas are aligned for engaging one another and securing the shells of the carrier in the closed position. A detent or indented lock or clip is used to secure the two halves of the carrier together.

An alternative carrier comprises two semi-cylindrical elongated members mated together, an opening at each end of the carrier, and an insert to secure the product in place. The openings allow for insertion of the product into the carrier without requiring removal of the carrier from the carousel.

A sensor (e.g., an electronic computer controlled sensor) is included within the cavity formed between the two halves of the carrier. That sensor is capable of ascertaining the release of any materials from within the vessels contained within the carrier. For example, the sensor could detect liquids or gasses that should not normally be present within the carrier. In accordance therewith, the sensor can activate a lock or warning light or signal, that alerts the carrier handler that something has been released within the water/air tight carrier, and that special care must be taken before opening the carrier. Alternatively, the control system could direct the defective carrier to a predetermined "safe" location.

While a plastic carrier is functionally equivalent to conventional steel, aluminum or cardboard carriers in some respects, plastic has the unique characteristic in that it has a certain "memory" for its original shape. That is, if twisted, struck or otherwise subjected to abuse, the plastic of the carrier of the present invention will tend to return to its original shape. In contrast, metal or cardboard carriers, when subjected to heavy use, are frequently permanently bent or distorted, thus detracting from their geometric symmetry and reducing their useful lives. Conventional carriers which are deformed in this way do not maintain a good air seal in the pneumatic line nearly as well as does the present invention. Also, conventional carriers which have been bent or distorted frequently open in the carrier line during use, thus necessitating the closure of the pneumatic tube system as aforesaid.

There are numerous criteria used in designing a carrier for pneumatic systems. It is preferable that the carrier be light, inexpensive and foolproof. Also, the carrier should be arranged so that it cannot be entered into a tube system when in an open position or open while in the tube. Such an arrangement ensures that the carrier is closed before it is entered into the system thereby limiting the possibilities that the carrier contents will be lost in the system and that the carrier will become lodged in the system. The carrier should preferably also be capable of carrying a maximum length of materials around given bends in the system and be capable of being locked in a closed position. A pair of ring seals (referred to also as accelerator, glide or travel rings, etc.) should be provided intermediate the ends of the carrier for guiding the carrier through a pneumatic tube system and for limiting air seepage past the carrier. End portions of the carrier should be tapered to terminate in bumpers and a pair of latches are coupled to the shells for retaining the carrier in a closed position. A lock is provided for combining with the closed shells to prevent unauthorized opening of the carrier.

Although the present invention relates to an automated system for use in hospitals to supply oral/solid or parenteral products, it is not limited to such use. Other expressions of its use include dietary, laboratory and central supply systems. Also, it may be used in the preparation and transportation of intravenous bags.

As an alternative, intravenous tubing could be directly linked between the hospital pharmacy and intravenous ports in the individual patient rooms. Additionally, motorized carts may be used for the delivery of larger pharmaceutical products from the pharmacy to the proper destination, as well as for the transport of the pneumatic tube carriers from the receiving station to the individual patients' rooms.

It will be appreciated that although the above description is limited to a one directional process (i.e. from product preparation to product delivery to patient), it is obvious that the invention can also operate in the reverse. That is, a prepared product or sample can be sent from any receiving station of the pneumatic tube system back to the hospital pharmacy, or to any other location within the hospital.

BRIEF DESCRIPTION OF THE DRAWINGS

The invention will be better understood with reference to the drawings, in which:

FIG. 3A shows a perspective diagrammatic representation of an automatic pharmacy distribution system for injectable products;

FIG. 3B shows a perspective diagrammatic representation of an automatic pharmacy distribution system for oral/solid products;

FIG. 3C shows an enhanced perspective diagrammatic representation of the automatic oral solid distributor shown in FIG. 3B for an automatic pharmacy distribution system for oral solid products;

FIG. 5 shows a pneumatic tube loading carousel with a capacity of 50 carriers, a 4 zone inbound and outbound line system;

FIG. 6 shows an overall view of a carrier suitable for use with the present invention;

DETAILED DESCRIPTION OF THE PREFERRED EMBODIMENT

Figure 1:
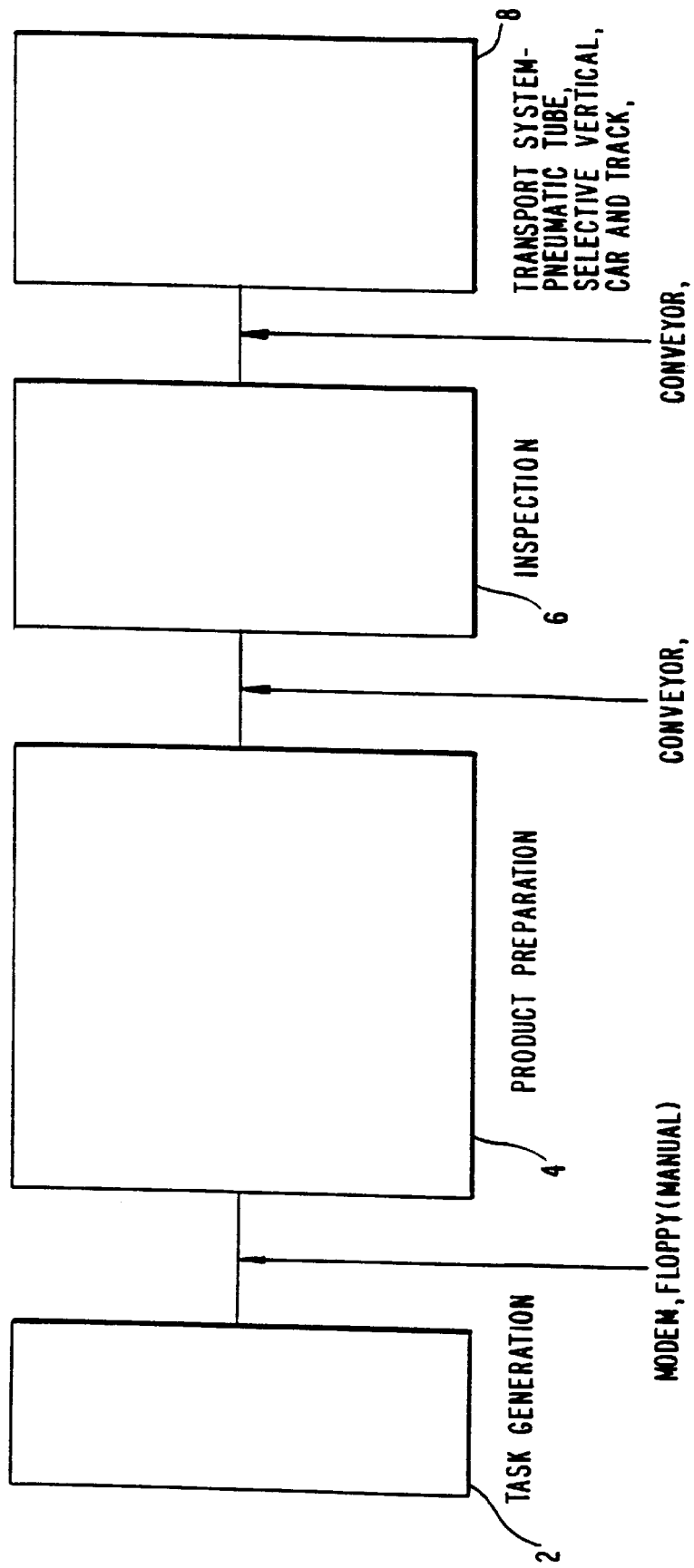
FIG. 1 shows functional block diagram of the entire invention.

Referring now to FIG. 1, an overview of the entire present invention is demonstrated in a functional block diagram. It shows input queue step 2 (or task generation step), product preparation step 4, inspection step 6, and transportation step 8.

Figure 2:
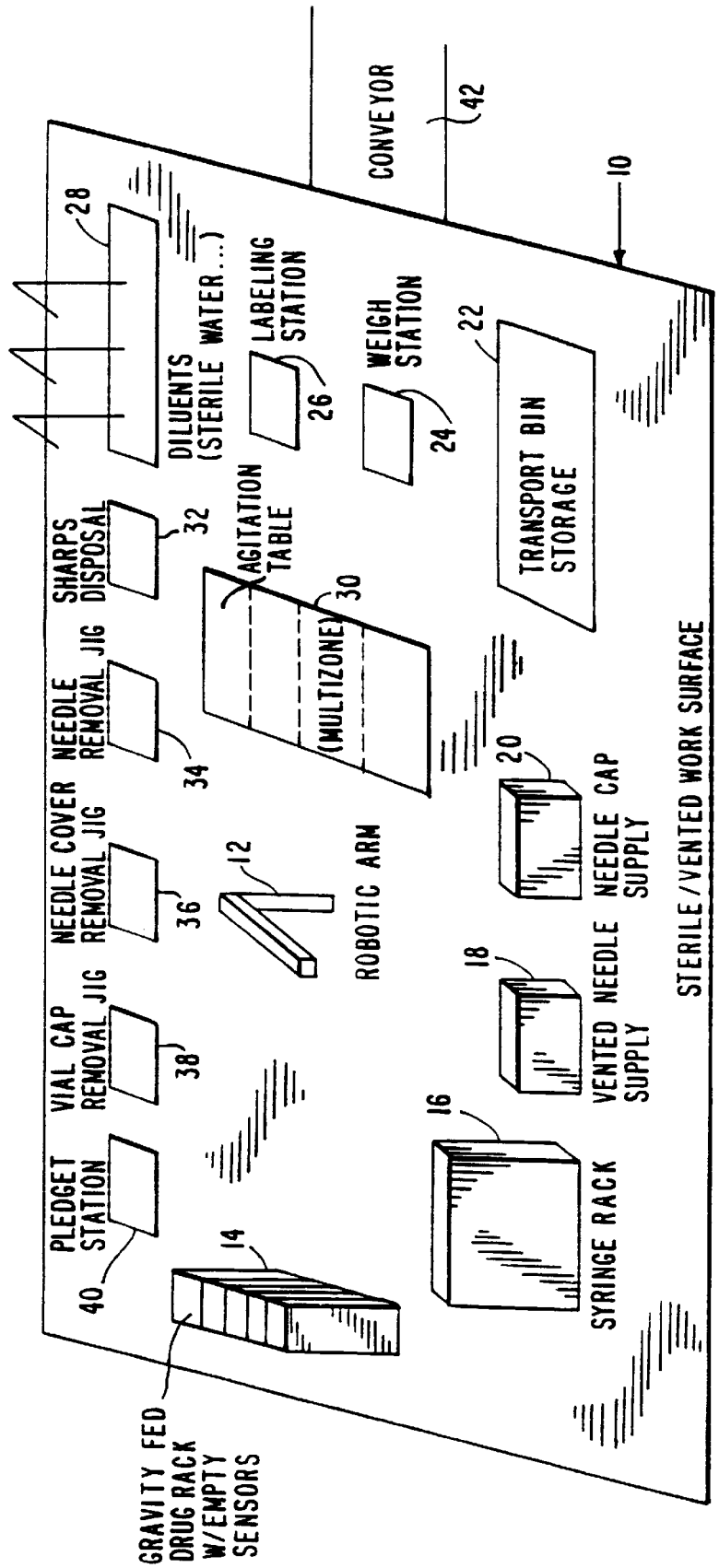
FIG. 2 shows a perspective diagrammatic representation of a selection, reconstitution, and dispensing apparatus.

Referring now to FIG. 2, the product preparation step is shown, and comprises a base 10 having thereon an industrial robot 12 which performs a series of manipulations resulting in the preparation of a single oral/solid or intravenous product unit based upon the information provided by the Pharmacy Information System. The robot 12 may have articulated arms, and gripping means in the form of jaw members having respective depending tangs at a rotatable wrist element of the arm.

Robot 12 may be arranged to present the jaw members at a number of stations including: gravity fed drug rack 14, syringe rack 16, needle supply rack 18, pledget station 40, vial cap removal jig 38, needle cover removal jig 36, needle removal jig 34, diluents rack 28, multi-zone agitation table 30, labeling station 26, weigh station 24, waste outlet 32, and transport bin storage 22.

The drug specified is retrieved by robotics arm 12 from gravity feed rack 14. A sensor located at the end of each column of the drug storage rack will detect an empty rack and notify the operation system that the column needs to be replenished.

With respect to oral/solid drugs, upon retrieval of the correct drug vial by the robotics arm 12, the protective cap is removed at removal jig 38 by inserting the vial into a removal jig 38 and snapping off the protective cap. The robotics arm 12 then brings the vial to another station where the appropriate dosage of oral/solid drug can be determined, for example, at weigh station 24, etc. Such dosage is removed from the vial via the robotic arm and placed into a delivery container. The delivery container is then put in a transport bin selected from transport bin storage 22. The bin with the product is then placed onto conveyor 42 which sends it to the inspection area.

With respect to parenteral products, upon retrieval of the correct drug vial by the robotics arm 12, the protective cap is removed, and the exposed rubber stopper of the vial is swabbed on an alcohol impregnated cotton pledget station 40. The pledget remains moist with isopropyl alcohol due to a wicking action.

After cleaning the stopper with alcohol, robot 12 sets the vial down, retrieves a standard 20 cc syringe with needle attached from syringe rack 16, and removes the protective needle cover by inserting it in needle cover removal jig 36 and pulling straight up. This action exposes the needle, and the protective cap is discarded.

Next, robot 12 inserts the needle into the injection port of a bag of Sterile Water for Injection from diluents rack 28. After insertion of the needle, the plunger on the syringe is extracted to the 20 cc mark, drawing in 20 cc of water into the syringe.

The syringe and needle containing the 20 cc is extracted from the Sterile Water for Injection bag on diluents rack 28. The regular needle is discarded in Sharps Waste Container 32 and a vented needle is retrieved from vented needle rack 18 and placed on the end of the syringe. The syringe is inverted and inserted into the selected vial of drug. The plunger is depressed, expelling the 20 cc of Sterile Water for Injection into the drug vial. The syringe and vented needle are removed, and the vial containing the diluent and drug are placed on agitation table 30 for sixty seconds.

Robot 12 proceeds to start on the next product while waiting for the current drug to complete the agitation step. Agitation table 30 is divided into zones relating to the zones in the pneumatic tube system.

Upon completion of agitation, the drug is removed from its zone of agitation table 30 and placed upon a compounding counter. The robot 12 then retrieves the appropriate syringe from syringe rack 16 and vented needle from vented needle rack 18, inserts vented needle into syringe, and inserts the syringe with needle into the vial of the drug in solution. The complete, attached system of drug vial, syringe and needle is inverted, with the drug uppermost and the syringe pointed upward. The plunger is retracted, withdrawing the entire contents of the drug vial back into the syringe. The syringe and vented needle are removed from the empty drug vial, and the empty vial is placed in a transport bin retrieved from transport bin storage 22, which is then fed to a staging location adjacent to conveyor 42.

The vented needle is removed from the syringe while in an upright position. This needle is placed in Sharps Waste Container 32. The syringe is inverted and a syringe tip cap is placed on the end of the syringe. The syringe with the reconstituted drug is labeled by rolling it over labeling station 26.

The labeled syringe with the reconstituted drug is placed on weigh station 24 and weighed to assure that the prepared unit meets anticipated specifications for weight, assuring that all diluent was added, and all drug extracted into the syringe. If accepted, the drug is placed in the same transport bin as the empty drug vial, and the transport bin is slid onto conveyor 42 which transports the product to the inspection station.

Figure 3:
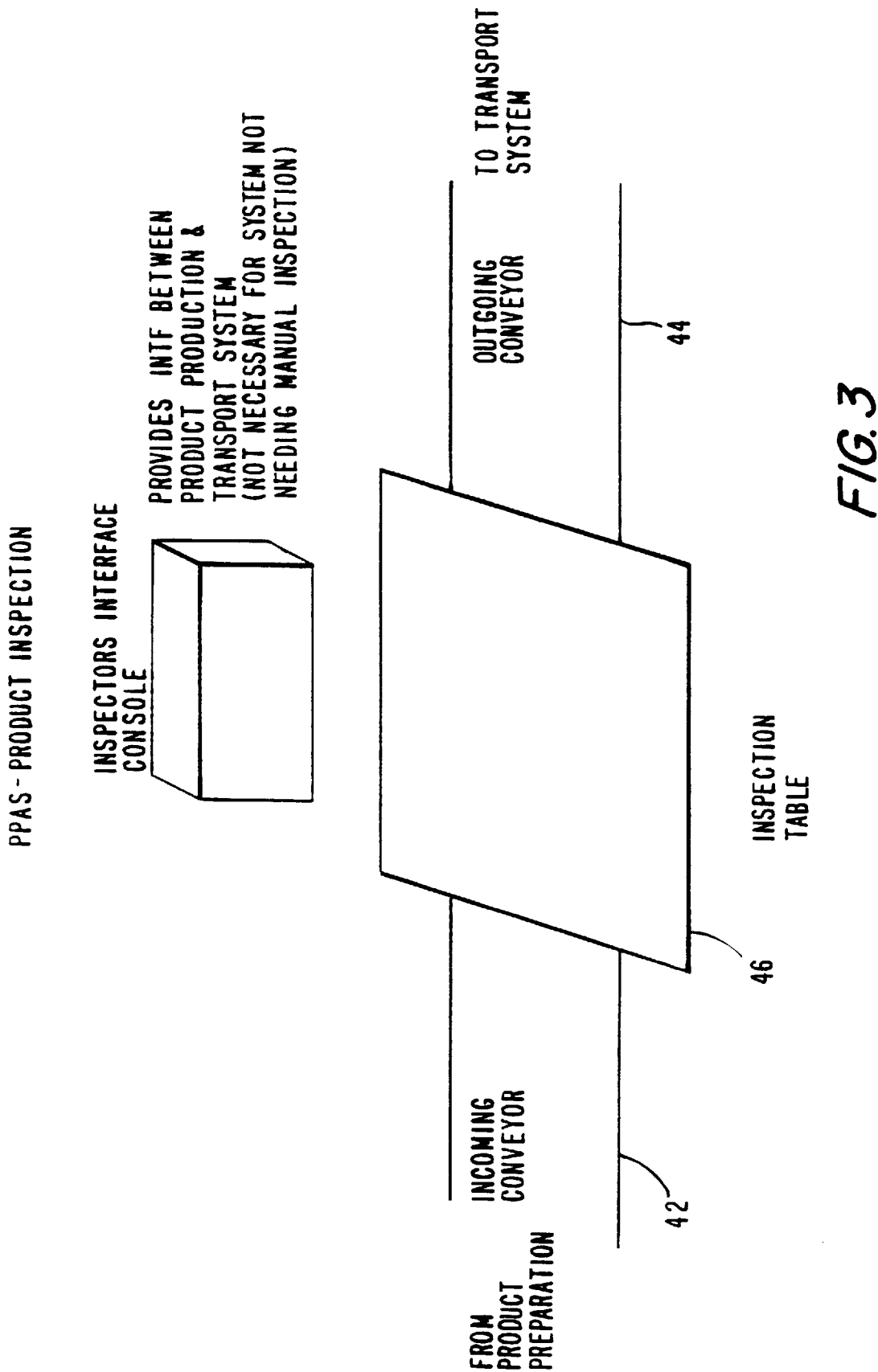
FIG. 3 shows a perspective diagram of the inspection station.

Now turning to FIG. 3, shown is the inspection station which can be either manual (i.e., by a highly skilled person) or automatic (i.e., barcode scanning, gas chromatography, and/or specific gravity measuring), where the product is sent after the appropriate drug is prepared, either oral/solid or parenteral. FIG. 3 shows incoming conveyor 42, inspection table 46, and outgoing conveyor 44. The product enters the inspection station via conveyor 42, wherein product is stopped on inspection table 46 to be either manually or automatically inspected. If approved, the product is placed in a transport bin which is placed on conveyor 44 leading to the loading dock of the pneumatic tube system.

FIG. 3A shows an automatic loading and inspection station for parenteral or injectable products to be loaded into carrier and sent to their destinations through the pneumatic tube system. FIG. 3A shows an automated system comprising a carrier opening stage 36, a carrier loading stage 38, and an inspection/closure stage 40. The empty carrier first enters the opening stage 36, after coming from the empty carrier storage and distribution system, where it is opened. The carrier is then moved to the loading stage 38 where the appropriate injectable product is automatically placed into the carrier. The injectable product is brought to the carrier via an incoming conveyor 42 from the product production station. The product enters the carrier through an opening in the top of the system. Once the product is loaded into the carrier, the carrier is moved to the third stage where the product and carrier are inspected. If approved, the carrier is closed securely and sent into the pneumatic tube system where it is delivered to the proper location.

Similarly, FIG. 3B shows an automatic loading and inspection station for oral/solid products to be loaded into carrier and sent to their destinations through the pneumatic tube system. Like FIG. 3A, FIG. 3B shows an automated system comprising a carrier opening stage 36', a carrier loading stage 38', and an inspection/closure stage 40'. The empty carrier first enters the opening stage 36', after coming from the empty carrier storage and distribution system 18, and is opened. The carrier is then moved to the loading stage 38' where the appropriate oral/solid product is automatically placed into the carrier. The oral/solid product is brought to the carrier via a robot system 42' (an enhancement of robot system 42' is shown in FIG. 3C) which selects the appropriate oral/solid product from a product storage station. The robot system 42' then inserts the oral/solid product into the carrier through an opening in the top of the system. Once the product is loaded into the carrier, the carrier is moved to the third stage where the product and carrier are inspected. If approved, the carrier is closed securely and sent into the pneumatic tube system where it is delivered to the proper location.

Figure 4:
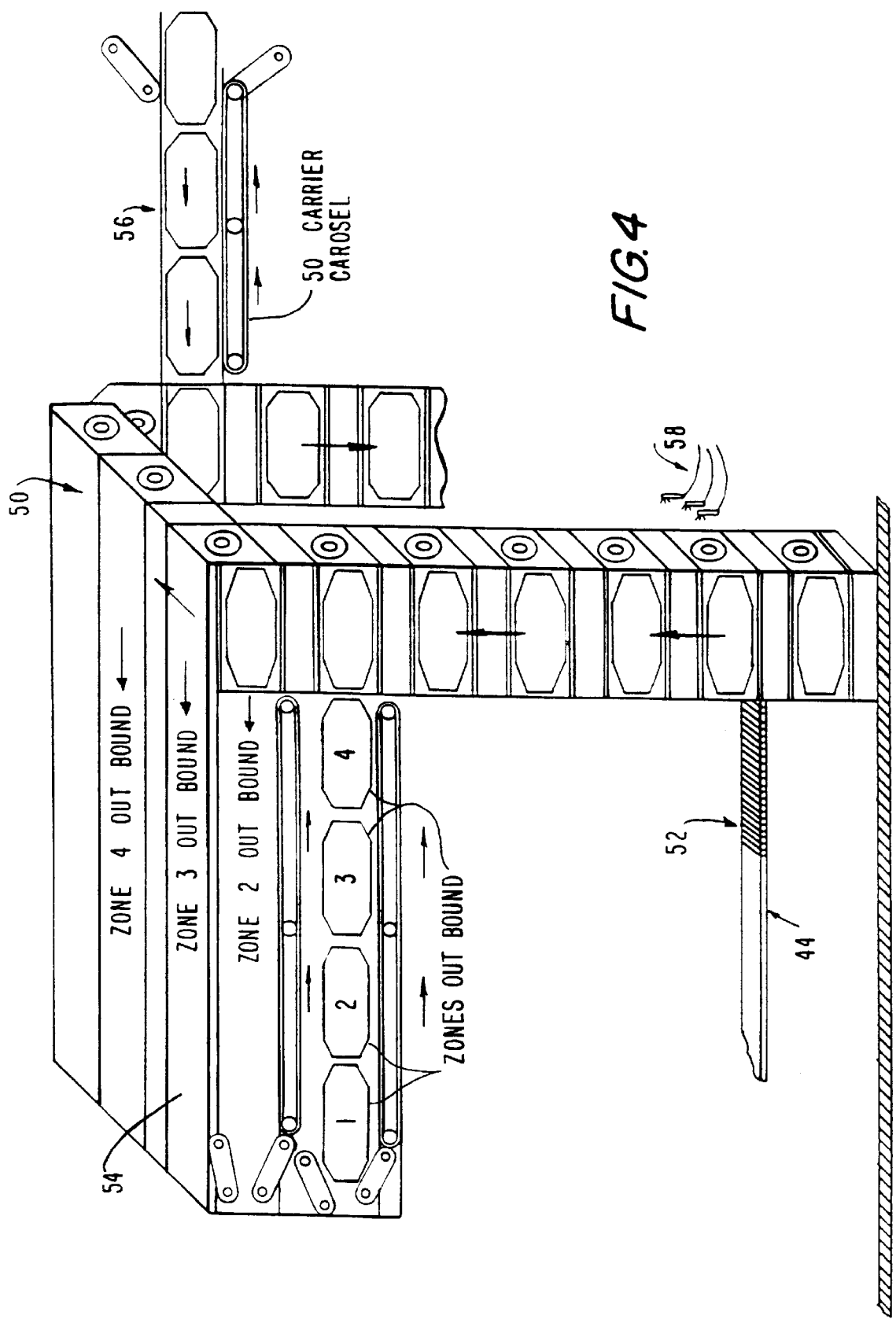
FIG. 4 shows a block diagram of the pneumatic tube carrier loading station using a turret style loader.

FIG. 4 represents a fifty carrier carousel loading station for the pneumatic tube system. It shows a fifty carrier carousel 50, conveyor 44, loading dock 52, four outbound tubes 54, four inbound tubes 56, and photo eyes 58. The transport bin containing the prepared product is transported to loading dock 52 via conveyor 44 from the inspection station. There a carrier 10 is presented to loading dock 52 as the fifty carrier carousel rotates past loading dock 52. A carrier 10 is presented to loading dock 52 in a closed position where photo eyes 58 verify that the carrier is the appropriate style carrier, that the carrier has an insert, and that the carrier insert is empty. If verified, the carrier 10 is removed from the carousel and the product is inserted into carrier 10. Carrier 10 is then inserted into an open member of carousel 50, which then rotates to the appropriate position to send carrier 10 containing the product to its proper destination via the pneumatic tube system.

However, if rejected, carousel 50 rotates so the photo eyes can check the next carrier, while keeping record of the rejected carrier and the reason for the rejection. This process continues until a useful carrier 10 is found. The system could notify the control system of the reject status of any carrier through a numbering or other labeling system distinguishing each carrier 10, and any rejected carrier 10 could be sent to a predetermined location to correct the defective condition.

FIG. 5 represents an alternative loading station for the system. It shows a loading device with a rotating turret 48. The transport bin containing the prepared product is transported to loading dock 52 via conveyor 44 from the inspection station. There a carrier 10 is selected from the rotating turret 48 after being verified as described above. Once verified, the carrier 10 is removed from turret 48 and the product is inserted into carrier 10. Carrier 10 is then inserted back into an open member of turret 48, which then rotates to the appropriate position to send carrier 10 and product to its proper destination via the pneumatic tube system.

Turret 48 can have a single rotatable turret with access to all zone of the pneumatic tube system, or it can have multiple rotatable turrets each corresponding to a single zone within the pneumatic tube system. Also, each turret can have the capacity to hold many carriers at a time.

In each of the above described loading systems (as shown in FIG. 4&5), a robot arm could be used as the means for removing the carrier from the turret, inserting the product into the carrier, and returning the carrier to the appropriate turret opening. Further, in the case of syringe products, a plunger style loading system could be used wherein the robot arm or other device can insert the syringe into the appropriate carrier through an opening in its end without having to remove it from either the turret or the carousel.

Once the product and carrier are loaded, the carousel rotates to the appropriate outbound pneumatic tube. Four of such tubes could be used in this invention, one for each zone in the system. The carrier is then inserted into the tube and then sent to its predetermined destination. A series of diverters present in the system allow inter-zone communication, thus allowing the pneumatic tube system to be used for station to station delivery.

Figure 6B:
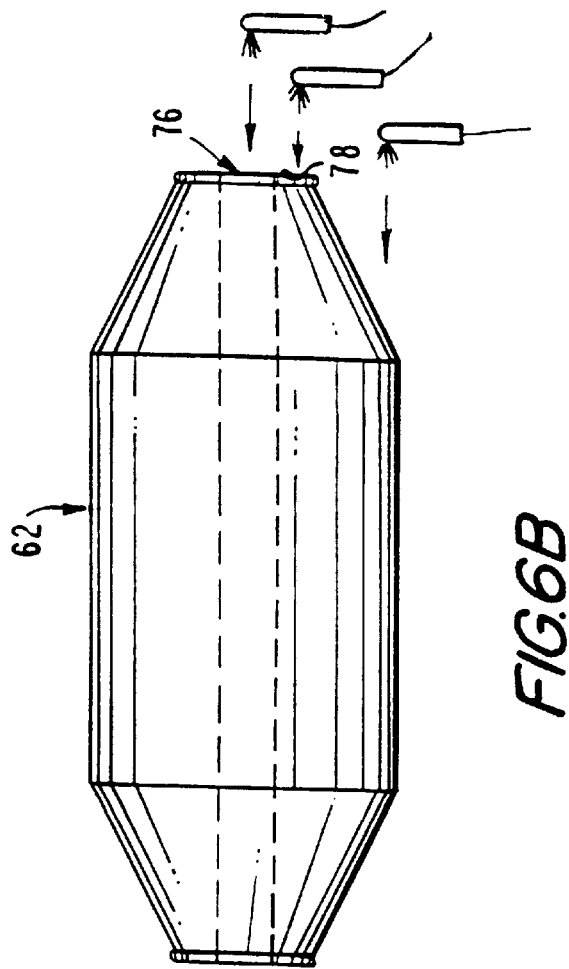
FIG. 6B shows a side view of a preferable carrier for this invention.
Figure 6A:
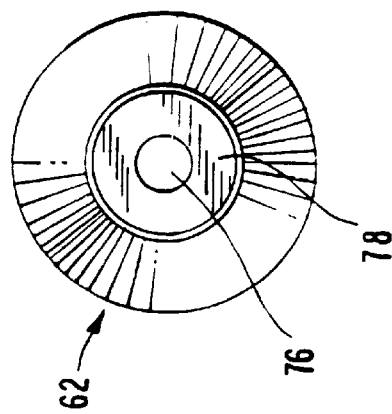
FIG. 6A shows an end view of a preferable carrier for this invention.

FIG. 6 is an overall view of carrier 60 preferred for use with the present invention. It shows carrier 60 consisting of first and second shells 62, 62' which extend longitudinally and which are interconnected by hinges 64 and rod locking members 68. Members 68 lock the rod in place, so that hinges 64 can provide for the opening and closing of the carrier 60 halves 62 and 62'. The carrier 60 halves 62 and 62' are formed of plastic, for example, and raised areas are formed along the exterior surface, around the transverse perimeter of the carrier, as shown as glide or travel or accelerator rings 66. Two accelerator or glide or travel rings 66 are use for each carrier 60, and may consist of Velcro® secured plastic or rubber strips. A suitable felt material or Neoprene® material may also be used to make the seals 66, which may also be cut from a sheet of the material such that moisture will tend to cause dimension changes substantially in the direction longitudinal with respect to the carrier, rather than radially. The seals 66 may be adhesively attached to the shells 62 and 62' at respective raised portions. The purpose of the rings 66 is so that carrier 60 forms a tight, consistent and secure fit within the interior of the carrier tubes, so that the carrier 60 may travel effectively through the carrier tubes. As the carriers 60 often reach speeds in excess of 25 feet per second, the rings 66 serve to form an air barrier around the carrier 60, so that the carrier 60 does not jam. Also, by minimizing air leakage around the carrier, rings 66 can minimize the air required to propel carrier 60. Felt insert is provided, as well, so that the rings 66 appear as continuous concentric circles—and no air can escape the seal the rings 66 form in relation to the interior of the carrier tubes, even where the hinge assemblies 64 are concerned. Ends of the carrier are defined by respective resilient bumpers 72. Each of the bumpers 72 is preferably larger than half the diameter of the pneumatic tube to avoid possible jamming of one carrier 60 with a second carrier within the pneumatic tube. The shells 62 and 62' are substantially identical in shape and are preferably molded in the same or a similar mold form from a suitable plastic material such as LEXAN® (a trade mark for a polycarbonate plastic sold by GE Plastics). Because the shells 62 and 62' are substantially identical and can often be made from even the same mold, molding costs can be significantly reduced.

In order to simplify this description, parts of shell 62 will be described, but it should be understood that corresponding parts of shell 62' also may exist, as desired. The shell 62 is generally semi-cylindrical over the major portion of its length, with the exception, for example, of the raised portions under rings 66. Those raised portions may also correspond to internally concaved zones, which may contribute to the overall structural integrity of the carrier 60.

The portions of carrier 60 that support the seals 66 are positioned intermediate the ends of the carrier 60 at positions which maximize the available length and diameter dimensions of the carrier. The shells 62 and 62' further includes tapered or frusto-conical end portions 70.

Hinge assemblies 64 are preferably molded as a part of the shells 62 and 62' and the pivot points of the hinges 64 are offset from mating edges of the shells 62 and 62' to permit the ends of the rings 66 and shells 62 and 62' to securely mate together when closed, without damage to the seal halves 66. The hinges 64 are preferably located so that they will not contact the interior of the carrier tube walls. Although the carrier tube walls are often made of steel, and the carriers 60 are often made of plastic, it is generally desirable to have only smooth, continuous surfaces contacting the interior of the carrier tube walls. For example, if a metallic hinge 64 were to scratch the interior of the carrier tube wall, ruts could result, which will facilitate air seepage, and a loss of system efficiency, as air passes through said ruts.

Figure 7A:
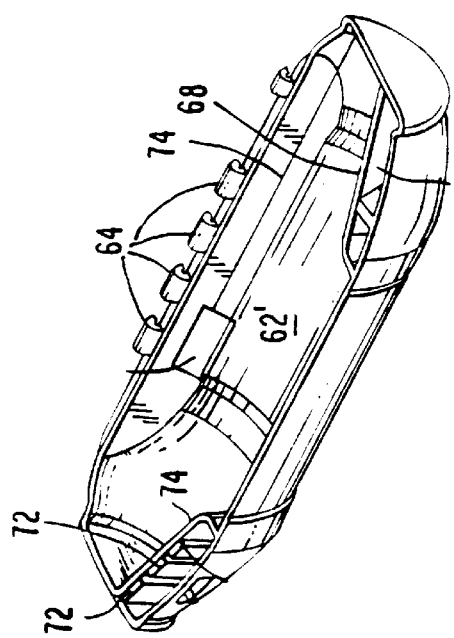
FIG. 7A shows a perspective view of the interior of one half of a preferable carrier for use with the present invention.
Figure 7C:
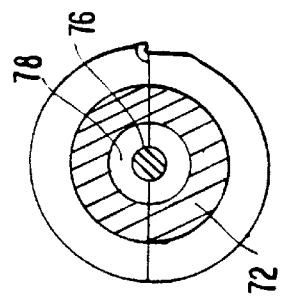
FIG. 7C is an end view of a carrier for use with the present invention, which shows an end bumper, and an end opening which allows the photo eyes to detect the contents of the carrier.
Figure 7D:
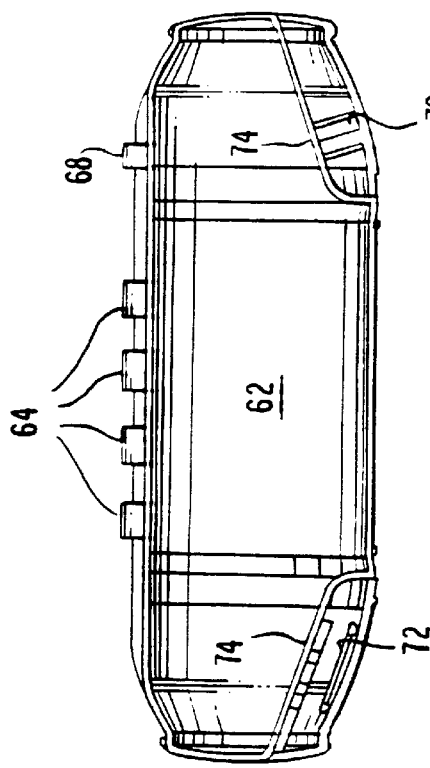
FIG. 7D shows a plan view of the interior of one half a preferable carrier for use with the present invention.
Figure 7B:
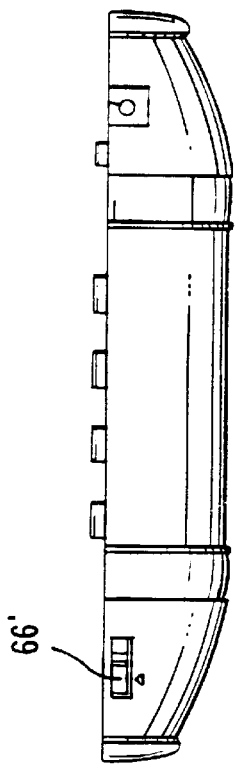
FIG. 7B is a side view of a half of a carrier for use with the present invention, which shows a latch to lock the carrier in its closed position, and an indicator for signalling conditions interior to a carrier.

FIG. 7A shows the interiors of both halves (62 and 62') of a preferred carrier 60 for use with the present invention. FIG. 7B is a side view of a half of a carrier 60 according to the present invention, which shows a latch 66' to lock the carrier 60 into its closed position, and an indicator for signalling conditions interior to a carrier 60. FIG. 7C is an end view of a carrier 60 according to the present invention, which shows the bumper, and openings 76 and 78 for use with the photo eyes.

Shells 62 and 62' form an internal cavity when closed together. That internal cavity is the usually the entire reason why the carrier 60 exists in the first place. However, certain exceptions may exist. For example, carrier 60 may be not a cavity bearing carrier at all, but rather a sophisticated monitoring vehicle, which contains video or other sensors, to inspect the interior workings of a pneumatic system. In that case, carrier 60 would be sent through a tube system, and could transmit or record information indicative of the interior walls of the pneumatic tube system. More usually, the carrier 60 with its internal cavity in place will be used to carry articles between remote points.

Carrier 60 is capable of carrying papers, such as drawings, business documents, cash, X-ray negatives and other similar items. Carrier 60 is often used to carry vessels, wherein the vessels often contain liquid, solid or gaseous materials that should ideally remain within the vessels. That is, the carrier 60, which moves at high speeds, is often used to carry vessels that contain various liquid substances, which are prone toward leaking out of the carrier 60, if the vessels should break within the carrier 60, or should the vessels become opened in transit (because, for example, a rubber stopper was not securely seated in the first place, or otherwise failed). Specifically, when the carrier 60 is used within the hospital environment, problems can result when vessels break or open within the carrier 60. The vessels in hospitals often include test tube with rubber stoppers, intravenous ("IV") bags, blood samples, viral or bacteria cultures, chemicals or other drugs, medicines, acids, or other materials that must be controlled or contained at all times.

Indeed, the vessels may even contain biohazardous materials, such as HIV infected blood, cultures of various viral infections, toxic chemicals such as cyanide, and other similar chemicals.

Naturally, whenever fragile objects (such as glass test tubes) are to be placed in the carrier 60, these objects are typically mounted in a container or retaining unit, which has been formed to fit snugly within the cavity defined by the interior surfaces of shells 62 and 62', thereby limiting the possibility of damage to the contents as the carrier passes through the pneumatic tube system. To safeguard against the leakage of such materials, and others, the carrier 60 according to the present invention has been designed with an internal perimeter wall 74. Perimeter wall provides an additional layer of protection against exposure to the outside world.

Perimeter wall 74 outlines the entire perimeter of carrier 60—more specifically, the boundaries of shells 62 and 62', as set forth in FIG. 7A. Also as shown in FIG. 7A, projections and receptors 72 (on both shells 62 and 62') are adapted to engage each other, as opposed on the opposing shells 62 and 62'), to retain the shells 62 and 62' in a closed position as shown in FIG. 6, with the use of detent latches or locks (not shown). The projections 72 have respective inclined leading faces for deflecting the projections radially inwards as the shells 62 and 62' are brought together. As the shells 62 and 62' move into a closed position, the projections and receptors 72 move radially outward into respective openings, to retain the shells 62 and 62' in the closed position. One major advantage of this arrangement is that the closing of the shells 62 and 62' is a natural action and requires no teaching. Anyone wishing to close the carrier 60 will naturally bring the shells 62 and 62' together resulting in a snap-action as the detent or interlocking latches move into their mating openings. Respective longitudinal edges of the shells 62 and 62' define interlocking recesses and projections indicated generally by the numerals 72. These edges locate the shells 62 and 62' relative to one another when the shells are in the closed position. Also, because of their shape, the projections/receptors 72 align corresponding edges of the shells on closing the carrier and also prevent closing the carrier unless the contents are entirely inside the shells. Further advantages of these projections 72 include increased torsional stability because of the interlocking arrangement; and an incidental advantage that because a carrier which is not completely closed will not fit into a pneumatic tube, an operator is forced to ensure that none of the contents project out of the carrier.

In use, it will be evident that unless the shells 62 and 62' are closed, the carrier 60 cannot be entered into a pneumatic tube. This is a significant advantage of the carrier because in the past, if carriers are entered into a tube without first closing the carrier, the result may be to lose the contents of the carrier 60 within the pneumatic tube system or in fouling the system to the extent that it no longer functions satisfactorily. Once the shells 62 and 62' are brought together so that the projections 72 engage in respective openings, the carrier 60 can be locked by inserting a key in, for example, a tumbler lock 66' (shown in FIG. 7B) and turning a key, or setting a combination. The carrier 60 can then be opened only by further use of the key. However, reference is again made to FIG. 7B to describe the lock switch 66'. Alternatively, only authorized persons having a key for an actual lock 66' could be established, to open the carrier, for example, if a controlled substance such as morphine is 10 contained within the carrier 60.

As shown in FIG. 7B, latch switch (or lock) 66' is used to depress the detent locking mechanism, so that the shells 62 and 62' can be separated, and the carrier 60 opened. Locking latches 66' are provided for retaining shells 62 and 62' in the closed position. In addition, electronically activated locks with pins (not shown) may be disposed between shells 62 and 62', so that latch switch 66' may be overridden, or defeated, so that the user of a carrier 60 will not open it if a vessel has become opened or broken in travel. To facilitate this function, an indicator is provided on the exterior of the carrier 60. The indicator is connected to internal sensor unit. The indicator will serve to inform the user that a spill or leak has occurred within the cavity of carrier 60. When the sensor unit detects the presence of a leak or spill (blood, gas, chemicals, liquids, etc.), the indicator, which may be a digital display, LED, or even an RS 232 communications port, will inform the user or an external computer, that something has become uncontrolled within the carrier 60. Then, proper precautions may be taken when opening the carrier 60. For example, if toluene has become released within carrier 60, the sensor will identify it as such (via, for example, gas chromatography), and will output its result to the indicator. Then, the indicator, which may be an LED, series of LEDs (which may indicate, for example, the severity of the interior condition), or an RS 232 port, can then output the result to a computer (not shown). In automated carrier tube systems, the carrier could even inform the receiving station (the opening to the vacuum tubes) of the condition, so that a user will be presented by, for example, a warning light, so that they will not open the carrier 60 until, in the case of toluene, the carrier 60 is brought to a ventilation hood, so that hazardous fumes may be vented safely away.

It will be appreciated that although the above parenteral products automation system description is limited to use in a hospital, the invention is not limited to such use. For instance, if found suitable, the invention could be used in other businesses or enterprises. While the foregoing embodiments of the invention have been set forth in considerable detail for the purposes of making a complete disclosure of the invention, it will be apparent to those of skill in the art that numerous changes may be made in such details without departing from the spirit and the principles of the invention.

Figure 8:
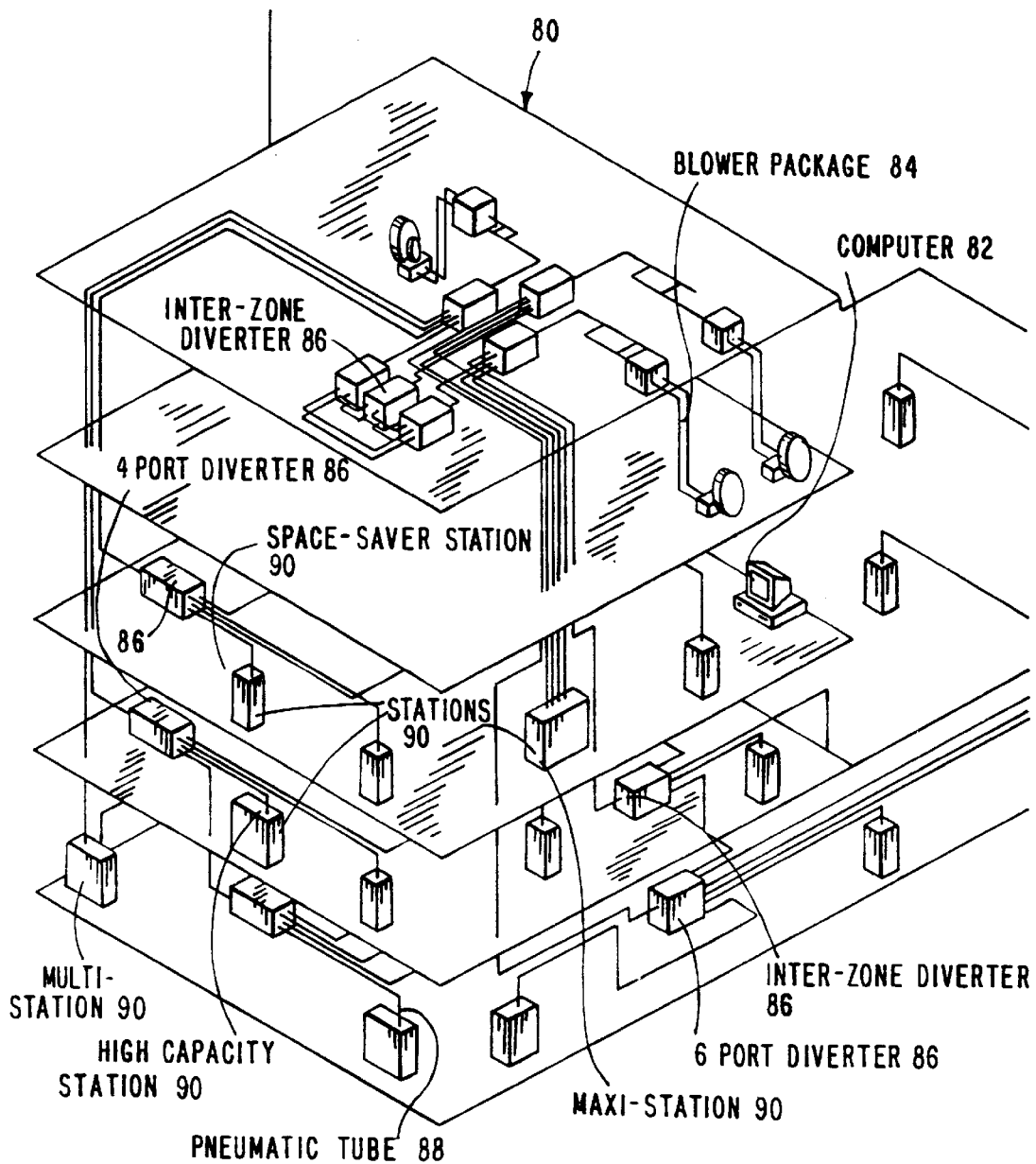
FIG. 8 is a perspective diagrammatic representation of a multi-zone pneumatic tube system.

FIG. 8 is an overall view of a pneumatic tube system 80. It shows a three-zone system comprising one blower package 84 per zone, pneumatic tubes 88, inter-zone diverters 86, computer 82, and receiving stations 90, all connected via single transmission tubing. Carriers move through the system shown in FIG. 8 under vacuum or pressure as supplied by blower package 84. As the carriers move through the system, the diverters 86 change position to change the direction of the carrier. Also, diverters 86 make inter-zone communications possible.

Although FIG. 8 demonstrates a three zone system with a limited number of receiving stations 90, a system with numerous zones and virtually unlimited stations 90 is possible.

It will be appreciated that although the above description is limited to a system for use in a hospital pharmacy, the invention is applicable for other similar purposes. For instance, the invention may be used with dietaries, laboratories, central supply areas, etc. While the foregoing embodiments of the invention have been set forth in considerable detail for the purposes of making a complete disclosure of the invention, it will be apparent to those skilled in the art that numerous changes may be made in such details without departing from the spirit and the principles of the invention.

We claim:

1. An automated system for the retrieval and delivery of oral products, said system comprising:
    at least one computer having a database capable of receiving and transmitting information within said system;
    a retrieval means comprising:
        at least one movable arm;

at least one pair of gripping means wherein said gripping means are attached to at least one of said movable arms having sensors wherein said sensors indicate the presence or absence of an object;

a supply station containing said oral products, wherein said supply station is positioned adjacent said retrieval means;

a plurality of pneumatic tube carriers;

a loading means for automatically loading said carriers into said pneumatic tube system; and a control means for coordinating transportation of said carriers containing said oral products through said pneumatic tube system to predetermined locations;

wherein said retrieval means is instructed by said computer to select said oral products from said supply station and insert said oral products into said pneumatic tube carrier.

2. A system according to claim 1, wherein said oral products are solids.

3. A system according to claim 1, wherein said oral products are liquids.

4. A method for the automatic retrieval and delivery of oral products through a pneumatic tube delivery system, said method comprising the steps of:

inputting information into said computer;

transmitting said information from said computer to said robot device and said pneumatic tube system;

selecting said oral product in accordance with said information;

inserting said oral product into a carrier; and transporting said carrier through said pneumatic tube system in accordance with said information;

wherein said computer controls said selecting and said transporting in accordance with said information, and wherein said robot device performs said selecting and said inserting.

5. A method according to claim 4, wherein said oral products are solids.

6. A method according to claim 4, wherein said oral products are liquids.

7. An apparatus for the automatic handling of oral products for delivery to a predetermined location, said apparatus comprising:

at least one computer;

at least one storage device;

at least one robot device;

at least one transporter;

at least one pneumatic tube carrier; and at least one pneumatic tube delivery system;

wherein said robot device selects and grasps said oral products from said storage device; wherein said transporter transports said robot device between said storage device and said pneumatic tube carrier system; wherein said robot device inserts said oral products into said pneumatic tube carrier; and wherein said oral products are selected and transported in accordance with signals generated from said computer.

8. An apparatus according to claim 7, wherein an inspection station is located midway between said storage device and said pneumatic tube delivery system.

9. An apparatus according to claim 7, wherein said oral products are solids.

10. An apparatus according to claim 7, wherein said oral products are liquids.

* * * * *